United States Patent [19]

Ford

[11] 4,049,970
[45] Sept. 20, 1977

[54] PULSED RADIATION DETECTOR SYSTEM

[75] Inventor: Michael Alan Ford, Maidenhead, England

[73] Assignee: Perkin-Elmer Limited, Beaconsfield, England

[21] Appl. No.: 650,635

[22] Filed: Jan. 20, 1976

[30] Foreign Application Priority Data

Jan. 21, 1975 United Kingdom ............... 02485/75

[51] Int. Cl.² ........................................... G01N 21/38
[52] U.S. Cl. ................................................ 250/461 B
[58] Field of Search ............... 250/461 R, 461 B, 270; 356/85, 97, 98

[56] References Cited

U.S. PATENT DOCUMENTS 3,947,683 3/1976 Schultz et al. ........................ 250/270
3,975,098 8/1976 West ................................. 250/461 R Primary Examiner—Davis L. Willis
Attorney, Agent, or Firm—S. A. Giarratana; F. L. Masselle; J. D. Crane

[57] ABSTRACT

Disclosed is a fluorescence spectrometer having an intermittently activated sample irradiating source, such as a UV lamp, the periods of activation being short (e.g., 100 microseconds) in comparison to the intervening inactive periods (e.g., 20 milliseconds). Fluorescence radiation emitted by the sample is detected by a photomultiplier, the output signal of which is supplied to an integrating amplifier for utilization. A field effect transistor (FET) in the output circuit of the photomultiplier has its gate coupled to a control unit which determines the activation periods of the lamp and, in timed relation thereto, cuts off the FET to interrupt the output circuit during periods that the lamp is inactive. A dual channel fluorescence spectrometer is also described.

10 Claims, 2 Drawing Figures

PULSED RADIATION DETECTOR SYSTEM

BACKGROUND OF THE INVENTION

1. Field of the Invention

This invention relates to apparatus of the type wherein an object is subjected to bursts of radiation the duration of each of which is short compared with the dwell time between successive bursts and the radiation as affected by the object is sensed for the purpose of deriving, for example, a signal representative of the nature of said object or merely a control signal for the activation of some utilization device or system. The invention is particularly related to analytical instruments such as fluorescence spectrometers in which the source for exciting fluorescence in the analytical sample is intended to operate in an intermittent or flash mode.

It is to be understood that, for the purposes of this description, an object may be said to affect the radiation falling thereupon if it acts on the radiation in any way, such as by re-directing it, re-distributing it or reemitting it at a different wavelength. In the case of a fluorescence spectrometer, for example, radiation in the UV or near UV region of the light spectrum would in fact be re-radiated by the object at a wavelength within the characteristic fluorescence spectrum of the object.

For literary ease and to facilitate a clear understanding of the invention, its general concept will be described in the context of a fluorescence spectrometer. This will not only enable the essential features to be readily appreciated but will also suggest the applicability of the invention to analogous situations, not necessarily in the context of material analysis.

2. Description of the Prior Art

In a known fluorescence spectrometer having a source of excitation radiation operating in the flash mode, the fluorescence of the sample substantially coincident with the duration of each excitation flash is analyzed by scanning it with a travelling continuous interference filter, at a slow enough rate of displacement relative to the flashing frequency to include a conveniently large number of flashes in one complete scan travel, the scan output being detected with a photomultiplier and finally integrated for presentation on a chart recorder. To mitigate the effect of radiation source fluctuations on the recorder output, a reference photomultiplier is used in addition to the sample photomultiplier and their respective outputs are ratioed. This scheme works well but cannot cope with the spurious responses introduced by unavoidable out-of-balances between the two outputs in terms of photomultiplier dark current characteristics, stray light, etc.

These out-of-balances are particularly significant in the prior art fluorescence spectrometers referred to, wherein the intermittency of excitation with periods of excitation very short in comparison intervals between flashes means that the signal content of each photomultiplier output is of a very short duration compared with the content due to the standing dark current between successive signals. The problem stems from a mode of operation that in other respects has been found most satisfactory, particularly in terms of instrument simplification. In the flash mode, instead of a radiation source continuously run at the high power levels of electrical energization required to ensure a continuum of radiation adequate for spectroscopic purposes, a compact gas-discharge lamp is used that is pulsed at high-peak power in bursts of a few microseconds. In order to ensure an acceptable lamp life, a comparatively long dwell period (typically some 20 milliseconds) must be tolerated between successive flashes; this exacerbates the problem.

SUMMARY OF THE INVENTION

For the solution of the problems of the prior art as outlined above, the present invention contemplates apparatus of the type referred to, comprising a source of radiation and a radiation detector. Means, including control means, are provided to cause the source to emit radiation flashes, the duration of each of which is short compared with a dwell time allowed between two successive flashes. A utilization channel is associated with the detector and switching means, operative in timed relation with said control means, make the detector output or electrical quantity derived therefrom available in the utilization channel during successive activation periods only each of which periods includes a flash duration and is also short compared with said dwell time.

As applied to overcome the particular problem of the out-of-balance in the prior art dual channel fluorescence spectrometer referred to earlier, the invention contemplates gating simultaneously, by means of a gating pulse just long enough to include with some margin the duration of the fluorescence decay, the outputs of the two photomultipliers to the respective amplifiers so that the amplifiers are only active during the useful fluorescence emission, which is very nearly coincident with the excitation flash, and are, therefore, only affected by the photomultipliers out-of-balances that occur during the gating pulse, which is very short compared with the dwell time allowed between gating pulses.

Exemplary embodiments of the invention in fluorescence spectrometers will now be described with continued reference to the annexed drawings.

DESCRIPTION OF THE PREFERRED EMBODIMENT

Figure 1:
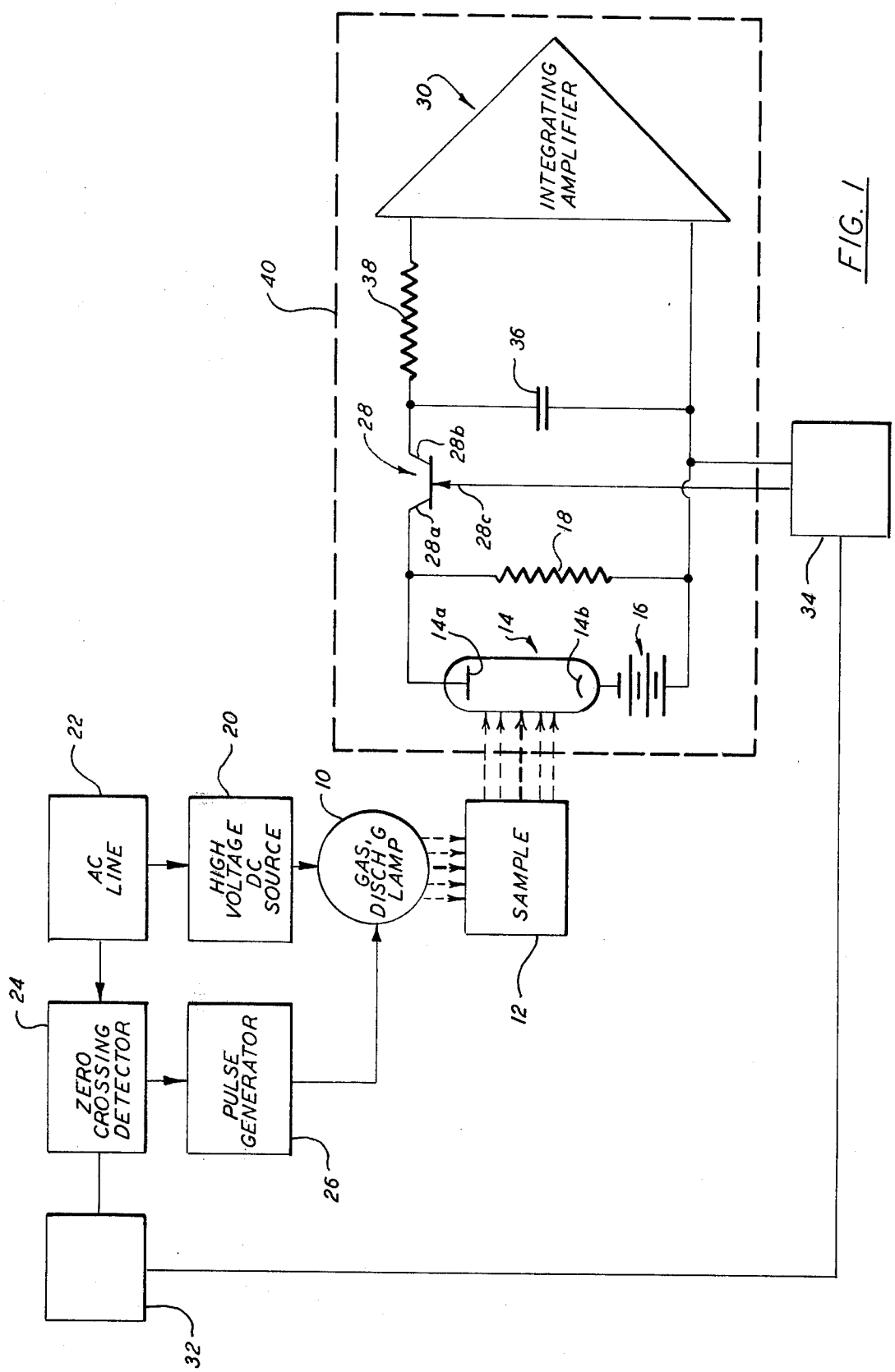
FIG. 1 is a combined schematic and block diagram of a single channel fluorescence spectrometer embodying the present invention.

In FIG. 1, a source of radiation, represented by a Xenon-filled gas-discharge lamp 10, is arranged to irradiate an object, represented by an analytical sample 12. A radiation detector in the form of a photomultiplier 14 or the like picks up the fluorescence resulting from the excitation of the sample 12, but is substantially screened from the direct rays of the source 10. Photomultiplier 14, which has an anode 14a and photocathode 14b, is part of a series circuit including a DC supply 16, providing an accelerating voltage of approximately 1kV, and a load resistor 18 of 100 kilohms. A steady current (referred to as dark current) flows through the resistor 18, and consequently, a small standing potential difference appears between its ends, when the photomultiplier 14 is in darkness. Energization of the lamp 10 in the flash mode is effected by the output from a high voltage DC source 20, e.g., by periodic discharge of a capacitor (not shown) incorporated with and re-charged by source 20, which rectifies electrical power supplied by the 50 Hertz AC lines 22. Radiation flashes from lamp 10 cause the sample 12 to emit fluorescence flashes that are almost coincident in time with the excitation flashes; photomultiplier 14 responds by generating a corresponding succession of current pulses superimposed on the dark current level, each pulse being separated in time from the next by a dwell period which, in relation to the peak energization power to which lamp 10 is subjected during the capacitor discharge, is chosen so as to ensure an acceptable lamp life.

It has been found that if the duration of an excitation flash is limited to a few tens of microseconds, say, some 20 to 30 microseconds, and the lamp 10 is flashed at a line frequency of 50 Hertz, enough power can be put into each flash to cause the plasma produced in the lamp by the capacitor discharge to emit a continuum of exciting radiation in the UV and near UV region of the light spectrum adequate for fluorescence spectrometer analysis, without curtailing the life of the lamp to an unacceptable extent.

The timing of the excitation flashes is expediently arranged by causing the capacitor of source 20 to discharge through the lamp 10 when a zero crossing in the AC waveform of lines 22, say, from the positive to the negative half-wave, is sensed by a zero crossing detector 24 and as a result, a sharp firing pulse is produced by a pulse generator 26 which is coupled to the firing electrode of lamp 10, detector 24 and generator 26 forming part of the control means.

If the arrangement so far described were put into operation, a series of transient signals would appear across the load resistor 18 each of which would be characterized by a peak voltage value, attained within very few microseconds of the initiation of an excitation flash, followed by an exponential tailing off. Each transient signal would last slightly longer than the excitation flash but it would be well contained within less than 100 microseconds, which still represents a very short interval compared with the nominal 20-millisecond dwell (actually 20 milliseconds minus transient signal duration) between successive transient signals.

Of course, some form of measuring channel (representing the utilization channel) is required in order to evaluate the signal voltage produced across resistor 18 and translate it into a value representative of fluorescence intensity. In the prior art fluorescence spectrometers referred to earlier, the photomultiplier signal is fed directly to an amplifier, which therefore responds to the dark current voltage occurring during the dwell periods, as well as the signal voltage with the attendant problem already discussed.

In accordance with the present invention, the signal developed across resistor 18 is coupled to an integrating amplifier 30 through switching means including a suitably controlled gate, such as an N-channel field effect transistor (FET) 28, having drain 28a, source 28b, and gate 28c, with the object of routing only the signal pulses to amplifier 30 and excluding the standing (dark current) voltages. It is necessary, therefore, to determine the time relation to the radiation source control means of a gating pulse for controlling the gate of FET 11 as well as the width of the pulse.

From what has been said earlier about the nature and the duration of the fluorescence decay, a 100-microsecond pulse is suitable and it must preferably be initiated just ahead of the excitation flash. To this end, a signal is derived from zero-crossing detector 24 which just before the rise of the firing pulse in generator 26 will cause the leading edge of a square gating pulse to be generated by switching over a monostable device in unit 32 having a 100-microsecond dwell, the trailing edge of the gating pulse being generated as the monostable device switches back to the stable state.

It is, of course, well known that if a FET is operated at a drain-to-source voltage below the cut-off voltage ($V_p$), it can be used as a low-level switch in what is usually the triode region; FET 11 is in fact intended to operate in such a region.

In the case of an N-channel device (which is usually preferred because electrons are more mobile than holes), a negative gate voltage (i.e., gate negative with respect to source) numerically greater than $V_p$ will keep the channel between drain and source in a cut-off condition and a voltage well below $V_p$ will open the gate. In the triode region, the change over from one to the other condition is very fast.

The 100-microsecond gating pulse available from unit 32 may now be routed to gate control unit 34, wherein means may be provided for keeping the gate terminal 28c of FET 28 at a cut-off negative potential and for causing the potential to approach zero upon the leading edge of the gating pulse occurring. Naturally, as the trailing edge of said pulse appears, a return to the cut-off state is established. It follows that FET 28 is kept in the "on" state for 100 microseconds, beginning from an instant just before the lamp 10 fires. The whole of the fluorescence decay is, therefore, represented in the signal routed to the amplifier 30.

Insofar as the fluorescence decay signal can only extend over 100 microseconds and the time gap between successive signals is just under 20 milliseconds, there is ample scope for introducing a suitable RC time-constant ahead of amplifier 30. In FIG. 1, this time constant is represented by the presence of a shunt capacitor 36 and the series resistor 38. This provision lessens the speed of response requirements of amplifier 30.

In a manner which will be described presently with reference to FIG. 2, the basic layout enclosed in broken line block 40 may be duplicated to form a dual channel arrangement wherein the additional photomultiplier acts as a reference by responding to a suitably attenuated value of each light flash. The amplified photomultiplier outputs may then be ratioed so that as to cancel the effect of any drift in the light output of the source 10. Gate control unit 34 is shown outside block 40 because it would in fact be common to both the sample and the reference channels.

Figure 2:
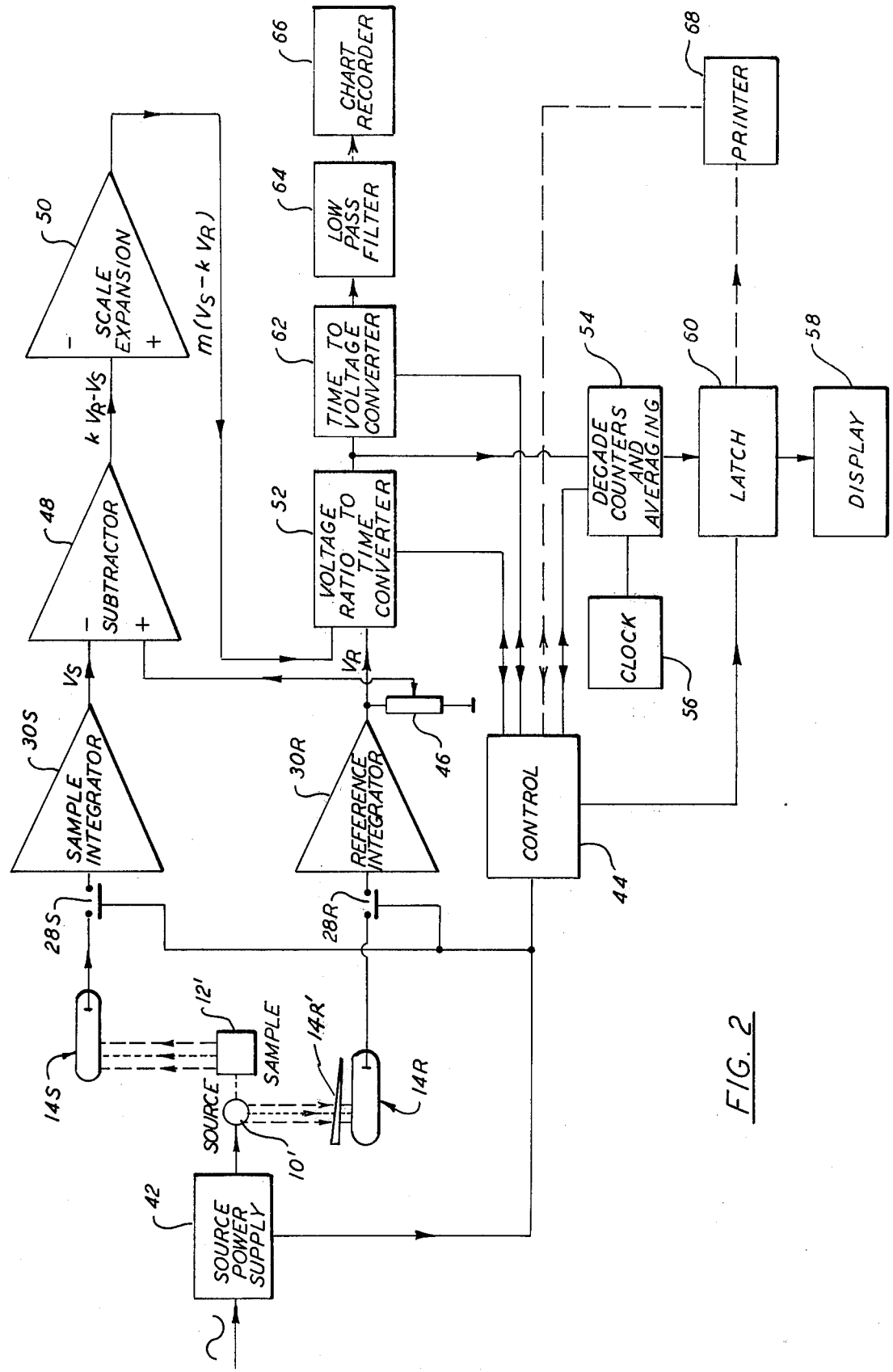
FIG. 2 is a block diagram of a dual channel fluorescence spectrometer in accordance with the present invention.

FIG. 2 illustrates a block diagram representing the application of the invention to a dual channel fluorescence spectrometer. It will be noted that a sample integrating amplifier 30S and a reference integrating amplifier 30R are shown. The portion of the diagram to the left ahead of amplifiers 30S, 30R is merely a very schematic representation of what has already been described with reference to FIG. 1. Briefly, it shows a power supply unit 42 representing in fact the functions described with reference to units 20, 22, 24, 26, 32 and 34 in FIG. 1, a gas-discharge lamp 10', a sample 12', a sample photomultiplier 14S, a reference photomultiplier 14R with associated radiation flux attenuator 14R', a sample signal gate 28S, and a reference signal gate 28R. The only additional circuitry represented in said portion of the diagram is for routing of a signal derived from the gating pulse for gates 28S and 28R to a control unit 44, through which the logic of the system to be described is established.

Continuing the reference to FIG. 2 with s to processing the signals generated in the two channels, it may be arranged for the incremental inputs to integrating amplifiers 30S, 30R, respectively, to be summed every eight flashes of the flash source 10, so that a voltage level $V_s$ and a voltage level $V_R$ become available at the outputs of the amplifiers. A portion of voltage $V_R$ is tapped off by means of a potentiometer 46 and subtracted from $V_2$ in a subtracting amplifier 48. This cancels out the unwanted contribution to $V_s$ made by the fluorescence of the solvent where the sample is in fact a solution and by the cell containing the sample. The difference value from amplifier 48 is then multiplied by a scale expansion factor in a scale expansion amplifier 50. It should be noted that amplifiers 48 and 50 are both inverting, which means that the output of amplifier 50 is in fact $m(V_s - kV_R)$, i.e., the required difference between the sample signal and a fraction k of the reference signal miltiplied by the scale expansion factor $m$.

The output from the amplifier 50 and that from the reference integrating amplifier 30R are ratioed and the ratio converted to pulse width in converter unit 52, wherein a ramp generator may be used to produce a voltage pulse the time duration of which is proportional to the ratio of $m(V_s - kV_R)$ to $V_R$. Thus, at this stage of signal processing, fluorescence information is in the form of pulses the duration of which varies in accordance with the fluorescence intensity, the frequency being one pulse every 160 milliseconds. Four information pulses are summed and the time interval representing the sum measured in the counter and averaging unit 54. The measurement is effected by counting the number of clock pulses originating from clock 56 included in said sum. To this end, logic signals are passed between the control unit 44 and each of the units 52 and 54. The numerical value representing the sum is passed in binary coded data form to the digital display 58 through latch 60. Fluorescence readings are therefrom up-dated every 32 flashes which means that the display time is 0.6 second.

If desired, in order to achieve more refined measurements, eight, say, of the sums may be averaged over a 5-second period and displayed for a further 5 seconds.

The information pulses issuing from unit 52 may be converted to analogue voltage in unit 62 which after filtering in low pass filter 64 may be displayed as a trace by the chart recorder 66.

A possible additional facility, selectable at will, is represented by the printer 68, which, through the latch 60 under the control of unit 44, may receive the same binary coded information normally routed to the display 58.

It can now be appreciated that in the case of a fluorescence spectrometer in accordance with the present invention, there is a specific advantage to be gained in activating the photomultiplier output substantially coincidently with the excitation flashes and de-activating it during the dwell periods in that the contribution to the photomultiplier signal of any phosphorescence that happens to be given out by the sample under analysis becomes negligible.

What is claimed is:

1. A pulsed radiation detector system comprising, in combination:
   a. a source of electromagnetic radiation;
   b. an electromagnetic radiation detector;
   c. means, including control means, intermittently engaging said radiation source to cause emission of radiation flashes having a duration which is short in comparison to intervals between flashes; and
   d. switching means operative in timed relation with said control means for making available the detector output or an electrical quantity derived therefrom in a signal utilization channel during successive activation periods, each of which periods includes a flash duration and is also short compared with said intervals.

2. A pulsed radiation detector system comprising, in combination:
   a. a source of radiation for irradiating a sample to fluorescence;
   b. means, including control means, for intermittently energizing said radiation source to cause fluorescent emissions by said sample of radiation flashes having a duration which is short in comparison to the intervals between flashes;
   c. radiation detection means positioned to receive radiation from said sample and generate an output signal in response thereto;
   d. means coupling the output signal of said detection means to a signal utilization channel; and
   e. switching means associated with said coupling means and operative in timed relation with said control means to interrupt the coupling of said output signal to the utilization channel during periods substantially coinciding with the intervals between flashes.

3. The invention as defined in claim 2 wherein said apparatus is a fluorescence spectrometer; said utilization channel includes an integrating amplifier coupled to said detection means by said coupling means; and said switching means is an electronically controlled semiconductor switching device.

4. Apparatus according to claim 3 wherein said detection means includes a photomultiplier, and said switching means is a field effect transistor having its source and drain terminals in series with the output of the photomultiplier and its gate terminal coupled to said control means.

5. Apparatus according to claim 3 wherein:
   a. said detection means includes a photomultiplier in series with a DC source and a load resistance coupled in parallel with the photomultiplier and DC source;
   b. said amplifier has its input terminals coupled across said load resistance; and
   c. said switching means is a field effect transistor having its source and drain electrodes in series with one of the amplifier input terminals and its gate terminal coupled to said control means.

6. Apparatus according to claim 5 including a series combination of a resistor and a capacitor, the series combination being coupled across the input to said amplifier and providing a predetermined time constant.

7. A dual-channel fluorescence spectrophotometer, comprising:
   a. a source of radiation for irradiating a sample;
   b. means, including control means, for intermittently energizing said radiation source to cause fluorescent emission by said sample of radiation flashes having a duration which is short in comparison to the interval between flashes;
   c. sample photodetector means positioned to receive radiation from said sample and generate a sample output signal in response thereto;

d. reference photodetector means positioned to receive an attenuated radiation flux from said source and generate a reference output signal in response thereto;

e. respective sample and reference integrating amplifiers coupled to receive the output signals of said sample and reference photodetector means;

f. respective switching means coupled between the output of said photodetectors and input of said integrating amplifiers and operative in timed relation to and by said control means for substantially simultaneously interrupting the coupling between said photodetectors and amplifiers during periods substantially coinciding with said intervals between flashes; and g. means for ratioing the output of said amplifier to generate a signal substantially free from the effect of fluctuations in the radiation output of said source.

8. A dual-channel fluorescence spectrophotometer according to claim 7, wherein each of said photodetector means includes a photomultiplier, and said switching means comprise respective field effect transistors each having its source and drain terminals in series with the output of a respective photomultiplier and its gate terminals coupled to said control means.

9. A dual-channel fluorescence spectrophotometer according to claim 7, wherein:

a. each of said photodetector means includes a photomultiplier in series with a DC source and a load resistance connected in parallel with the photomultiplier and DC source;

b. each of said amplifiers has its input terminals connected across the load resistance of a respective photomultiplier; and c. said switching means comprise respective field effect transistors each having its source and drain terminal in series with one of the input terminals of a respective one of said amplifiers and its gate terminal coupled to said control means.

10. A dual-channel fluorescence spectrophotometer according to claim 9 including respective RC time constants associated with the inputs of said amplifiers.

* * * * *

UNITED STATES PATENT AND TRADEMARK OFFICE
CERTIFICATE OF CORRECTION

PATENT NO. : 4,049,970
DATED : September 20, 1977
INVENTOR(S) : Michael Alan Ford It is certified that error appears in the above-identified patent and that said Letters Patent are hereby corrected as shown below:

Column 5, line 1, after "with", delete "s" and insert in place thereof --regard--.

Column 5, line 9, delete "$V_2$" and insert in place thereof --$V_s$--.

Column 5, line 68, delete "engaging" and insert in place thereof -- energizing --.

Signed and Sealed this

Fourteenth Day of February 1978

[SEAL]

Attest:

RUTH C. MASON
Attesting Officer

LUTRELLE F. PARKER
Acting Commissioner of Patents and Trademarks